(12) United States Patent
Butterworth et al.

(10) Patent No.: US 9,494,539 B2
(45) Date of Patent: Nov. 15, 2016

(54) METAL DETECTOR FOR PRODUCTION AND PACKAGING LINES

(71) Applicants: Mettler-Toledo Safeline Ltd., Manchester, United Kingdom (GB); TNA Australia Pty Limited, Sydney, New South Wales (AU)

(72) Inventors: Daren Butterworth, Manchester (GB); Alfred Alexander Taylor, Sydney (AU); Darren Ken Alchin, Sydney (AU)

(73) Assignees: METTLER-TOLEDO SAFELINE LTD., Manchester (GB); TNA AUSTRALIA PTY LIMITED, Sydney (AU)

( * ) Notice: Subject to any disclaimer, the term of this patent is extended or adjusted under 35 U.S.C. 154(b) by 259 days.

(21) Appl. No.: 14/449,221

(22) Filed: Aug. 1, 2014

(65) Prior Publication Data

US 2014/0340099 A1    Nov. 20, 2014

Related U.S. Application Data

(63) Continuation of application No. PCT/EP2013/052754, filed on Feb. 12, 2013.

(30) Foreign Application Priority Data

Feb. 17, 2012  (EP) .................................... 12155954

(51) Int. Cl.
*G01N 27/72* (2006.01)
*G01R 33/12* (2006.01)
(Continued)

(52) U.S. Cl.
CPC .............. *G01N 27/023* (2013.01); *G01V 3/10* (2013.01); *G01V 3/107* (2013.01); *G01N 27/02* (2013.01); *G01R 27/267* (2013.01); *G01R 33/1215* (2013.01)

(58) Field of Classification Search
CPC .. G01R 27/00; G01R 27/26; G01R 27/2611; G01R 27/267; G01R 33/028; G01R 33/0283; G01R 33/1215; G01V 3/10; G01V 3/107; G01N 27/72; G01N 27/9033; G01N 27/02; G01N 27/023; B64G 1/366
USPC ....... 324/600, 649, 654, 200, 228, 239, 244, 324/259, 500, 513, 537, 71.1, 71.4, 76.11
See application file for complete search history.

(56) References Cited

U.S. PATENT DOCUMENTS 3,588,687 A * 6/1971 Kohler ................... G01V 3/108
                                                            324/243
4,866,383 A * 9/1989 Taliaferro ................ G01V 3/08
                                                            324/207.24

(Continued)

FOREIGN PATENT DOCUMENTS

| CN | 1834690 A | 9/2006 |
|---|---|---|
| CN | 101025442 A | 8/2007 |
| WO | 2006/037176 A1 | 4/2006 |

*Primary Examiner* — Hoai-An D Nguyen
(74) *Attorney, Agent, or Firm* — Standley Law Group LLP

(57) ABSTRACT

A metal detector (420) has a metallic enclosure (421) with entrance and exit apertures (430, 431) whose cross-sectional areas differ from each other. Inside the enclosure is a coil system with a transmitter coil (423) and first and second receiver coils (424, 425). The apertures and the coil system enclose a detection zone (428) around a travel path on which objects under inspection move. The asymmetric detection zone has a variable cross-section along the travel path and the coils differ in size from each other. The receiver coils are connected in series, but their windings are wired with the opposite sense of rotation relative to each other. Energizing the transmitter coil generates a primary electromagnetic field that induces a first voltage and a second voltage in the corresponding receiver coils. Despite the asymmetry, the respective voltages cancel each other when no metal is present in the object investigated.

19 Claims, 2 Drawing Sheets

(51) Int. Cl.
*G01N 27/02* (2006.01)
*G01V 3/10* (2006.01)
*G01R 27/26* (2006.01)

(56) References Cited

U.S. PATENT DOCUMENTS

| | | |
|---|---|---|
| 5,572,121 A | 11/1996 | Beswick |
| 5,663,642 A | 9/1997 | Rumberger et al. |
| 6,204,667 B1 | 3/2001 | Won |
| 6,822,171 B2 | 11/2004 | Bennett et al. |
| 7,061,236 B2 | 6/2006 | Britton |
| 7,791,337 B2 * | 9/2010 | Simon ............ G01V 3/104 324/219 |
| 7,893,690 B2 | 2/2011 | Simon |
| 2005/0206373 A1 * | 9/2005 | Kondo ............ G01V 3/104 324/239 |
| 2009/0058408 A1 * | 3/2009 | Linder ............ G01B 7/10 324/229 |
| 2014/0002067 A1 * | 1/2014 | Garces Cadenas .... G01V 3/081 324/228 |
| 2014/0125311 A1 * | 5/2014 | Butterworth ......... G01R 33/025 324/71.1 |
| 2015/0276964 A1 * | 10/2015 | McAdam ............ G01V 3/10 324/329 |

* cited by examiner

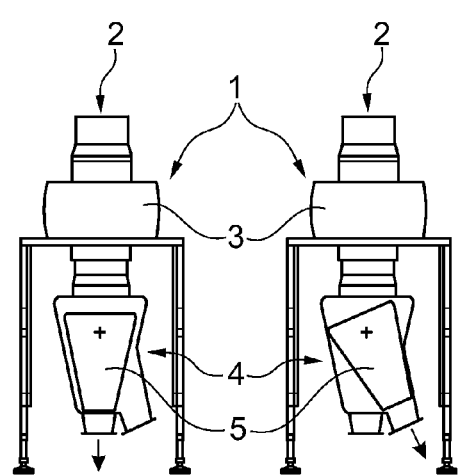
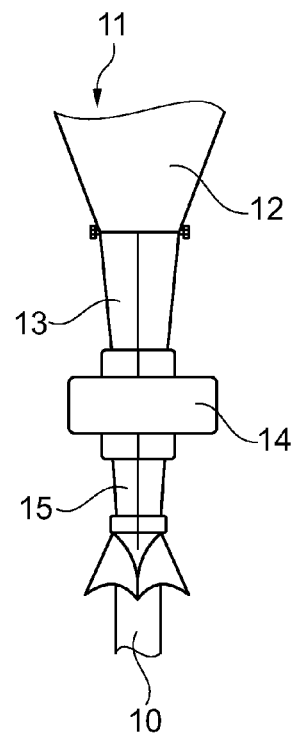
Fig. 1A Fig. 1B
Fig. 1 (PRIOR ART)
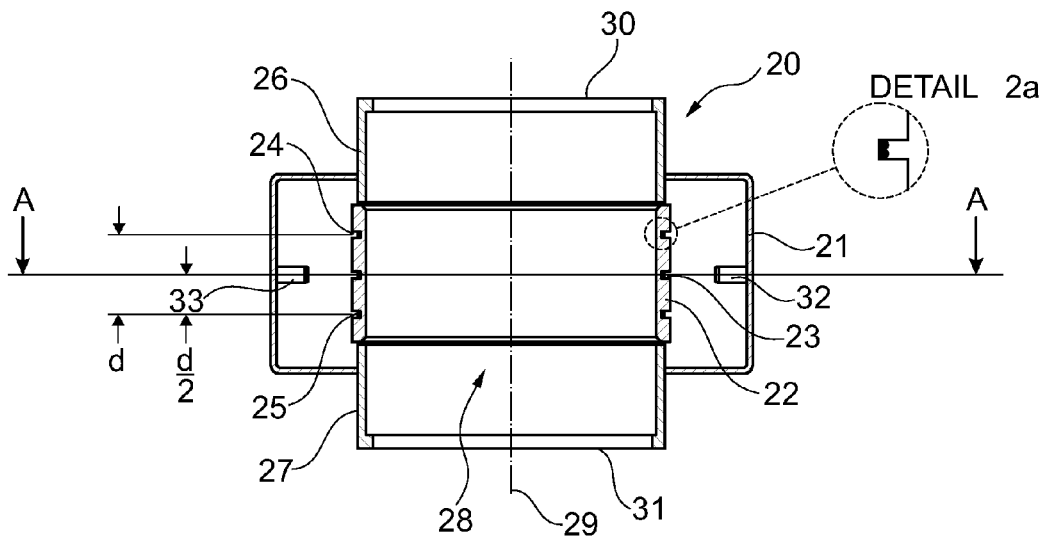
Fig. 2 (PRIOR ART)

METAL DETECTOR FOR PRODUCTION AND PACKAGING LINES

CROSS-REFERENCE TO RELATED APPLICATIONS

This application is a continuation of PCT/EP2013/052754, filed on 12 Feb. 2013, which in turn claims a right of priority under 35 USC §119 from European patent application 12155954.6, filed 17 Feb. 2012. The content of each application is incorporated by reference as if fully recited herein.

TECHNICAL FIELD

The invention relates to an industrial metal detector for the food-, beverage-, pharmaceuticals-, plastics-, chemicals-, packaging-, and other industries.

BACKGROUND OF THE ART

The main purpose of metal detectors of the kind described herein is to detect the presence of metal in an article, a bulk material, or generally any object being examined. Such metal detectors are widely used and integrated into production and packaging lines, for example to detect contamination of food by metal particles or components from broken processing machinery during the manufacturing process, which constitutes a major safety issue in the food industry. The generic type of metal detector that this invention relates to and which is known as balanced three-coil system with an encircling coil arrangement can be described as a portal through which the articles and materials under inspection are moving, for example individual packages riding on a horizontal conveyor belt through a vertical portal, or a stream of bulk material in free fall through a vertical duct or funnel passing through a horizontally arranged portal.

The portal is generally configured as a box-shaped metallic enclosure with an entrance aperture and an exit aperture. The operative part of the metal detector is a system of three electrical coils wound on a common hollow carrier or coil former made of a non-metallic material, which is arranged inside the metallic enclosure. The aperture cross-section of the coil former matches the size and shape of the entrance and exit apertures and lines up with them, so that the coil former and the entrance and exit apertures form a tunnel defining a detection zone through which the conveyor belt or other transport means moves the articles or materials under inspection. The aperture cross-section of this detection zone tunnel is generally rectangular or circular, but could also have any other shape.

In state-of-the-art metal detectors of this type, the coils are exactly parallel to each other and, consequently, their parallel planes are orthogonal to their common central axis. The center coil, also called transmitter coil, is connected to a high-frequency oscillator and thus generates a primary alternating electromagnetic field which, in turn, induces a first and a second alternating voltage, respectively, in the two coils on either side of the center coil, which are also called the first and the second receiver coil. The first and second receiver coils are connected in series with each other, but with their windings wired in opposition to each other. In other words, the coil wire runs continuously from a first output terminal through the windings of the first receiver coil, then with the opposite sense of rotary direction through the windings of the second receiver coil to a second output terminal. In addition the first and second receiver coils are located equidistant from the transmitter coil. Therefore, they are in all respects mirror images of each other in relation to the central plane of the transmitter coil, and thus the first and the second alternating voltage induced in them by the primary alternating electromagnetic field will cancel each other. In other words, the mirror symmetry of this state-of-the-art metal detector has the result that the voltage picked up between the first and second output terminals will be zero.

Symmetrical balance coil arrangements can also consist of multiple transmitter coils and/or multiple receiver coils that are arranged in such a way to achieve a so called null balance condition. Therefore the first receiver coil can form one or more entrance-side receiver coils, and the second receiver coil one or more exit-side receiver coils. Likewise the transmitter coil can be designed as one or more transmitter coils.

However, if a piece of metal passes through the coil arrangement, the electromagnetic field is disturbed, giving rise to a dynamic voltage signal across the output terminals of the serially connected receiver coils.

The metallic enclosure surrounding the coil arrangement serves to prevent airborne electrical signals or nearby metallic items and machinery from interfering with the proper functioning of the metal detector. In addition, the metal enclosure adds strength and rigidity to the assembly, which is absolutely essential as even microscopic dislocations of the coils relative to each other and relative to the enclosure can disturb the detection system which is sensitive to signals in the nanovolt range.

An issue of concern in metal detectors of the foregoing description is their sensitivity to stationary and, even more so, to moving metal in areas outside the detection zone and, in particular, even far outside the enclosure of the metal detector. This is due to the fact that the electromagnetic field generated by the transmitter coil extends outside the entrance and exit apertures to a distance as far as two or three times the length of the detection zone. If there are stationary or moving metal parts within this range, for example the support frame or other components of a conveyor, the interaction of the electromagnetic field with the metallic parts in its reach will produce an unwanted output signal of the receiver coils which interferes with the actual detection signals originating from metallic contaminants in the material under inspection traveling through the metal detector. Therefore, unless special design measures are taken, a large space before the entrance aperture and after the exit aperture of the metal detector has to be kept free of all metal. The area that must be kept free of metal is generally called the "metal-free zone" or MFZ.

A more detailed explanation of this requirement of a metal-free zone and a means for reducing or even eliminating the metal-free zone in the type of metal detector described hereinabove are presented in EP 0 536 288 B1, which is hereby incorporated by reference in the present disclosure. One of the possible means for reducing or eliminating the MFZ described in EP 0 536 288 B1 has the form of metallic flanges or collars that may be integral with the rims of the entrance and exit apertures of the enclosure of the metal detector. These flanges or collars act as short-circuit coils in which a current is induced by the alternating electromagnetic field of the transmitter coil. The induced current, in turn, generates a secondary electromagnetic field which can, under certain conditions, nullify the primary field of the transmitter coil beyond a certain distance before the entrance coil and after the exit coil, even to the extent that the primary field outside the apertures of the enclosure is almost totally suppressed and the metal-free zones before the entrance aperture and after the exit aperture are effectively reduced to zero and a so-called "zero metal-free zone" (ZMFZ) can be achieved.

A metal detector using the ZMFZ concept of the foregoing description is especially advantageous for situations where space is restricted, such as with a short conveyor system or when the metal detector is installed in a vertical flow path for example to inspect objects falling inside a chute from a weighing machine to a bag-making machine.

In the last-mentioned case of a vertical arrangement, the chute that guides the falling objects or materials under inspection through the metal detector is in many cases either funnel-shaped or includes funnel-shaped sections. A funnel or generally a conduit with a progressively narrowing cross-section does not match the cylindrical detection zone through a metal detector of the kind described previously. Thus, if the funnel-shaped conduit is matched to the entrance aperture of the enclosure of the metal detector, towards the exit aperture there will be an empty air space of increasing width between the tapered circumference of the funnel and the cylindrical inside wall of the detection zone. This arrangement may be considered sub-optimal in terms of detector sensitivity and space usage. More directly, it points to the need for a metal detector whose entrance and exit apertures and detection zone conform to a tapered, funnel-shaped profile of a channel or chute which guides the movement of the objects or materials through the metal detector. A solution to that need can be provided by an asymmetric configuration of the entire metal detector, wherein not only the exit aperture is smaller than the entrance aperture of the enclosure, but also the coils following each other in sequence, i.e. the entrance-side receiver coil, the transmitter coil, and the exit-side receiver coil, will have to be progressively smaller. At the same time, the advantages of the balanced coil system and of the ZMFZ design concept should preferably be maintained.

It is therefore the object of the present invention to provide a metal detector, for example of the generic type described in the introductory paragraph, with an asymmetrically configured enclosure and detector coil system while maintaining at least the functional properties of a balanced coil system.

SUMMARY

This objective is met by a metal detector having the features named in the independent patent claim 1. Various embodiments and refinements of the invention are presented in the dependent claims.

The metal detector according to the present invention has a metallic enclosure with an entrance aperture and an exit aperture and, arranged inside the metallic enclosure, a coil system with at least one transmitter coil and at least one first and at least one second receiver coil. The entrance and exit apertures and the first and second receiver coils enclose a tunnel-like detection zone through which objects under inspection are transported along a transport path that enters the metal detector through the entrance aperture and leaves the metal detector through the exit aperture.

The metal detector of the present invention is distinguished from known prior art by the fact that the cross-sectional areas of the entrance aperture and the exit aperture differ from each other and that the detection zone has a cross-sectional profile that changes continuously from the entrance aperture to the exit aperture. Consequently, since the coil system encloses the detection zone and thus conforms to the variable cross-sectional profile of the detection zone, the at least one first receiver coil, the at least one transmitter coil, and the at least one second receiver coil differ from each other in size.

The first and second receiver coils in a metal detector of the present invention are therefore not symmetric to each other relative to a plane defined by the at least one transmitter coil, but regardless of said asymmetry, the first and second receiver coils and the at least one transmitter coil are in a state of balance where the aforementioned first and second voltages cancel each other when there is no metal present in said objects under inspection, i.e. the at least one first receiver coil and the at least one second receiver coil are positioned relative to said at least one transmitter coil at an unequal distance.

As balance coil arrangements can also consist of multiple transmitter coils and/or multiple receiver coils that are arranged in such a way to achieve a so called null balance condition, in the context of the following description and claims of the inventive concept, the term "transmitter coil" and/or "receiver coil" shall stand for "at least one transmitter coil" and/or "at least one receiver coil".

Relative to this transport path, the first receiver coil can be arranged ahead of the transmitter coil, and the second receiver coil is arranged after the transmitter coil.

In preferred embodiments of the invention the first and second receiver coils and the transmitter coil are wound on a common coil former which is hollow, made of an electrically insulating non-metallic material, and whose inside conforms to the variable cross-sectional profile of the detection zone.

Preferably the first and second receiver coils are wired in series with each other, they have an equal small number of winding turns (typically a single turn), and they are wound with the opposite sense of rotation relative to each other.

As the metal detector of the present invention lacks the symmetry of the coil system that is common to metal detectors of the prior art, a new way has been found to balance the induced voltages of the first and second receiver coils. It was worked out that the smaller of the receiver coils should be nearer to the transmitter coil in order to equalize the induced voltages in the unequal receiver coils.

In an exemplary embodiment the transmitter coil is positioned in a central plane between the entrance aperture and the exit aperture and the receiver coils are arranged each at a different distance from the transmitter coil, i.e. asymmetrically with regard to their position from said central plane. Alternatively the at least one transmitter coil is positioned out of center between the entrance aperture and the exit aperture whereas the receiver coils are arranged each at a different distance from the transmitter coil but not necessarily from said central plane.

In a preferred embodiment of the invention, the detection zone has the shape of a funnel, so that the cross-sectional area of the flow stream continuously decreases from the entrance aperture to the exit aperture. The funnel can be shaped for example like an inverted truncated cone, a section of a hyperboloid or other surface of revolution, an inverted truncated pyramid, and other continuous as well as multifaceted surfaces of rotational symmetry.

In a preferred embodiment, the metallic enclosure is designed to approximately follow the shape of the funnel at a substantially uniform distance. For example, if the detection zone is cone-shaped, the enclosure could likewise be a truncated cone, concentric with and parallel to the coil former. Alternatively, a conical coil system could be installed in an enclosure with the shape of a truncated pyramid whose central axis coincides with the central axis of the coil former and whose walls can be sloped at the same or at a different angle as the circumference wall of the coil former.

Preferably, the space between the coil former and the enclosure is filled with a potting medium, for example a thermosetting polymer such as an epoxy compound. This helps to secure the coil former and coil windings as well as any electronic components against shocks and vibrations and also to exclude moisture.

Like the most closely comparable metal detectors of the prior art, a preferred embodiment of the metal detector of the present invention comprises means for cancelling the primary field beyond a distance from the coil system. The means for cancelling the primary field are preferably configured in the form of metallic flanges or collars that are connected to or integral with the rims of the entrance and exit apertures of the metallic enclosure of the metal detector.

The flanges or collars perform the function of short-circuit coils in which an alternating current is induced by the primary electromagnetic field of the transmitter coil. This induced current, in turn, generates a secondary electromagnetic field which nullifies the primary field of the transmitter coil beyond a certain distance from the coil system but does not affect the metal detector in its function of detecting metal contained in objects moving through the detection zone.

Preferably, the boundaries beyond which the primary field of the transmitter coil is nullified are located directly at the entrance and exit apertures of the enclosure. Thus, there are no zones adjacent to the metal detector that must be kept free of metal. In this preferred embodiment, the metal detector with an asymmetrically configured enclosure and detector coil system combines the functional properties of the balanced coil system and the ZMFZ design concept.

To produce a metal detector according to the invention with an asymmetrically configured enclosure and detector coil system, one could for example start with a tentative design that meets given dimensional specifications and represents a best estimate for meeting given performance specifications. Based on this initial design and using a finite element technique, the magnetic field could be numerically determined inside the detection zone as well as in the ambient space surrounding the metal detector. By further calculating the time derivative of the magnetic flux through the receiver coils one could estimate the voltage that would be induced in the receiver coil circuit not only in the absence of any metal in the detection zone, but also with simulated metallic test objects moving through the detection zone. In a process of iterative cycles, one would make modifications to individual parameters of the tentative design until the discrepancies found between the results of the computer model and the given target specifications for the metal detector are sufficiently reduced to meet given tolerances.

BRIEF DESCRIPTION OF THE DRAWINGS

The metal detector according to the invention will hereinafter be explained in more detail through examples and with references to the schematically simplified drawings, wherein:

FIG. 1 shows gravity feed inspection systems with a diverter device (1A) and with a vertical form fill seal (VFFS) bag maker (1B) with state-of-the-art metal detectors;

FIG. 2 represents a sectional view of a state-of-the-art metal detector for applications as illustrated in FIG. 1;

DETAILED DESCRIPTION

Figure 3:
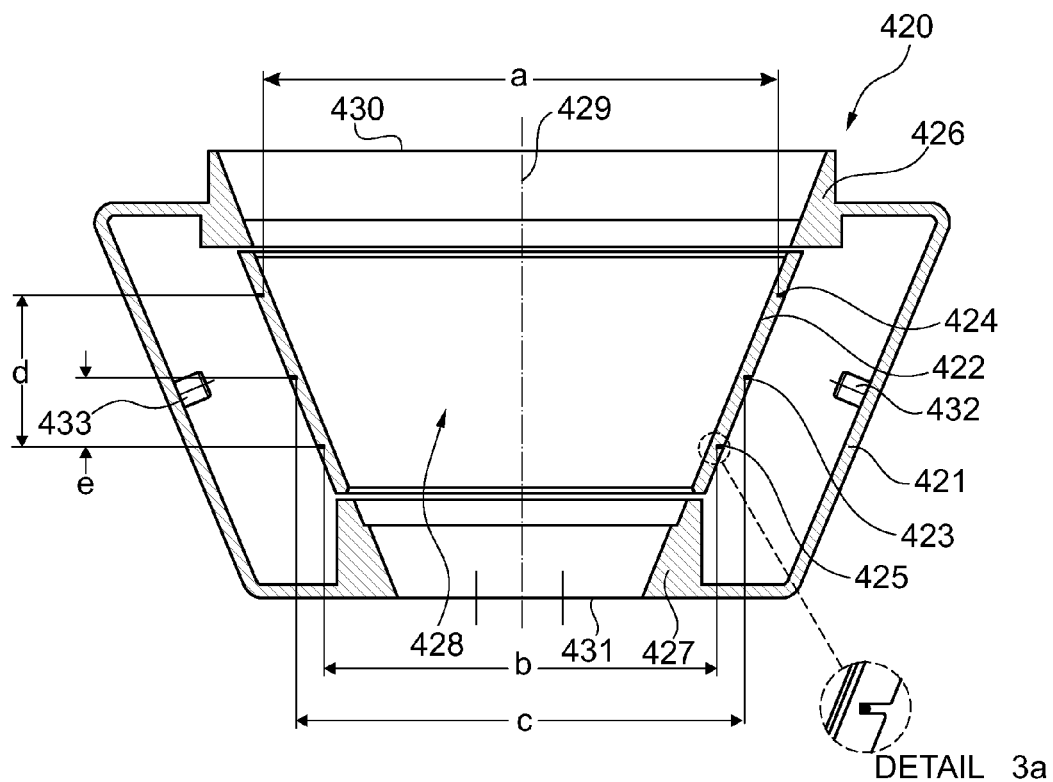
FIG. 3 represents a sectional view of a metal detector according to the invention.

FIGS. 1 and 2, which have been taken from a company publication, "Reduction of Metal Contamination", Mettler-Toledo Safeline © 2008, illustrate the state of the art in the field to which the invention pertains. The inspection system 1 in FIG. 1A serves to detect metal contaminations in a granular product 2 such as peanuts, rice, plastic pellets, milk powder, cocoa beans, etc. The product 2 passes in free fall through a state-of-the-art metal detector 3 (as described in detail in the context of FIG. 2) and then enters into a diverter system 4. As long as no metal contamination is detected, the diverter 5 in the shape of a slender funnel allows the product 2 to continue its fall in the vertical direction and to move on through the production line (not shown in the drawing). If metal is found to be present in the stream of product 2, an output signal of the metal detector 3 causes the diverter 5 to instantly switch position, so that the flow of product 2 is diverted to a separate destination for rejected product.

In the vertical form fill seal (VFFS) bag maker 10 of FIG. 1B, weighed portions of a product 11 to be packaged in bags are released from a weighing machine (not shown in the drawing) into a scale discharge chute 12 which directs the product to a plastic funnel 13. The funnel 13 concentrates the falling stream of product 11 to the aperture width of a state-of-the-art metal detector 14 (as described in detail in the context of FIG. 2). A plastic tube 15 continues to guide the falling product 11 through the metal detector 14 and to the VFFS bag maker 10 (only symbolically indicated).

FIG. 2 shows a sectional view of a metal detector 20 that is representative for the state of the art embodied by the metal detectors 3, 14 of FIGS. 1A and 1B, respectively. The principal parts of the metal detector 20, which incorporates the zero metal-free zone (ZMFZ) concept as explained previously herein and in more detail in EP 0 536 288 B1, are the enclosure 21, the coil former 22 with the transmitter coil 23 and receiver coils 24, 25, and the aperture flanges 26, 27. The coils 23, 24, 25 run in grooves of the coil former 22 as indicated by the enlarged detail 2a, and the rotary direction of the coil windings is reversed between the receiver coils 24 and 25. The enclosure 21 and the aperture flanges 26, 27 must be made of metal in order to perform their function of confining the primary magnetic field generated by the transmitter coil 23. The coil former 22, on the other hand, must be made of a non-conductive but mechanically stable material such as, e.g., a fiber-reinforced plastic. The coil former 22 and the aperture flanges 26, 27 form a tunnel-like cylindrical detection zone 28 through which a product under inspection (not shown in the drawing) moves for example in vertical fall in the direction of the central axis 29 (indicated by a dash-dotted line), entering the metal detector 20 through the entrance aperture 30 and leaving the metal detector 20 through the exit aperture 31. Also shown are bushes 32, 33 formed on the enclosure 21, which serve to mount the metal detector on a supporting structure. The cross-sectional profile of the enclosure 21 and/or the coil former 22 and aperture flanges 26, 27 can be round, but could also have any other shape, for example square or rectangular, as required by a given application for the metal detector. However, one fundamental property of the metal detector 20 and the entire state of the art that it represents is the mirror symmetry of the design relative to the plane A-A of the transmitter coil 23. The planes of the receiver coils 24, 25, with a distance d from each other, run parallel to and at an equal distance d/2 from the plane A-A. In addition to their exact mirror symmetry, the receiver coils 24, 25 are electrically fine-adjusted so as to balance each other and produce a zero output signal when no metal contamination is present in the product moving through the detection zone.

The aperture flanges 26, 27 act as short-circuit coils in which a current is induced by the alternating or pulsating primary electromagnetic field of the transmitter coil 23. According to Lenz's rule, an induced current always flows in such a direction as to oppose the field change that causes it. Accordingly, the secondary electromagnetic field generated by the induced current of the aperture flanges 26, 27 opposes the primary field. With appropriately designed and dimensioned aperture flanges 26, 27 the secondary electromagnetic field nullifies the primary field of the transmitter coil beyond a certain distance from the coil system—in particular ahead of the entrance and after the exit of the metal detector—but does not affect the metal detector in its function of detecting metal contained in objects moving through the detection zone.

Figure 4:
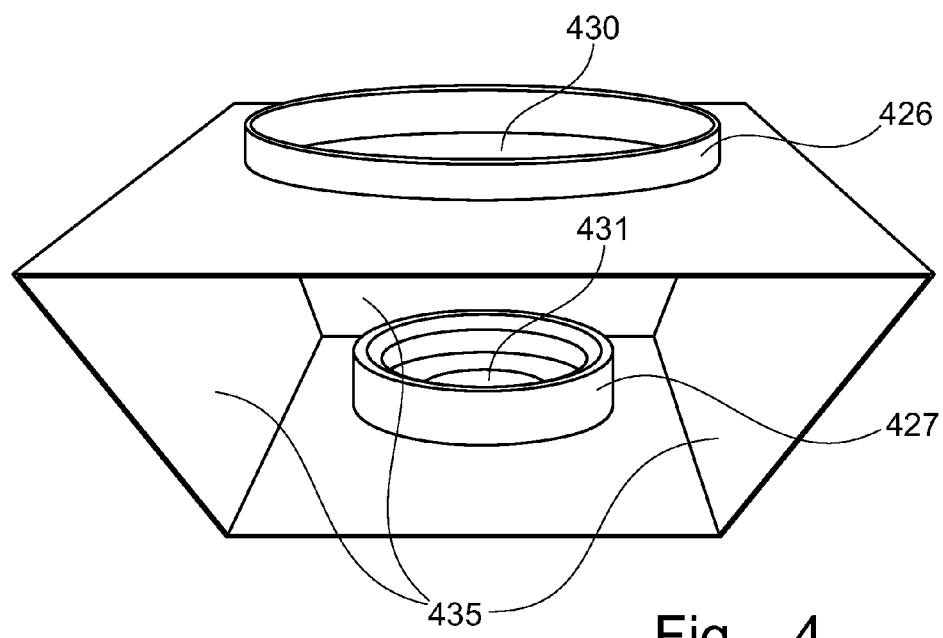
FIG. 4 represents a perspective view of the metal detector of FIG. 3.

FIG. 3 represents a metal detector 420 according to the invention in sectional view with a conically shaped detection zone 428 between entrance and exit apertures 430, 431 of different diameter. In FIG. 4 the enclosure 421 of the same metal detector 420 is shown in a perspective view. The metal detector 420 in FIGS. 3 and 4 and all of its components are functionally analogous to the metal detector 20 of FIG. 2. The fundamental difference lies in the conical shape of the detection zone 428 of the metal detector 420 as compared to the cylindrical detection zone 28 of the metal detector 20. In conformance to the conical detection zone 428, the coil former 422 and the insides of the aperture flanges 426, 427 are shaped and lined up with each other as three sections of a truncated cone with a central axis 429. The side walls 435 of the enclosure 421 in FIGS. 3 and 4 are trapeze-shaped and slanted at the same angle as the conical wall of the coil former 422, but this represents a design choice. The enclosure 421 could also for example be box-shaped or cylindrical. Also shown are bushes 432, 433 formed on the enclosure 421, which serve to mount the metal detector 420 on a supporting structure.

With the conical coil former 422, the receiver coils 424, 425 can of course no longer be equal in size, nor can their distances from the transmitter coil 423 be equal. By way of a qualitative explanation, if the receiver coils 424, 425 were placed at equal distances to either side of the transmitter coil 423, the magnetic flux traversing the smaller receiver coil 425 would be smaller than the magnetic flux traversing the larger receiver coil 424. In other words, the coil system would not be balanced. This imbalance cannot be corrected by increasing the number of winding turns in the smaller coil 425, as the impedance presented to the preamplifier in the receiver circuit needs to be closely controlled in order to maintain an optimum signal to noise ratio, which determines the inductance of the coils and, in particular, dictates a low number of winding turns in the receiver coils 424, 425, typically only a single turn as indicated in the circled detail 3a in FIG. 3. Therefore, in order to balance the receiver coils 424, 425, the transmitter coil 423 needs to be moved closer to the smaller receiver coil 425. In the illustrated example, with a distance d between the receiver coils, the transmitter coil 423 has been positioned at a distance $e<d/2$ from the smaller receiver coil 425. Accordingly, the diameter of the transmitter coil 423 is smaller than the average diameter of the receiver coils 424, 425, i.e. $c<(a+b)/2$. As mentioned previously, the exact position of the transmitter coil 423 between the receiver coils 424, 425 as well as the geometric details of the housing and aperture flanges can be determined with the help of a computer model through a process of iterative modifications until given requirements in regard to the balancing of the coil system, the cancelling of the primary field outside the metal detector, and the detection sensitivity to metal objects moving through the metal detector have been met within specified tolerances.

In the perspective drawing of FIG. 4, the trapeze-shaped enclosure wall 435 on the side that faces the viewer is removable, so as to allow the installation of the coil former and, possibly, sensitive parts of the electronic circuitry associated with the detector such as for example a preamplifier circuit connected to the output of the receiver coils 424, 425. After installation, the empty space between the coil former and the enclosure walls is filled with a potting compound and the removed sidewall 435 is put back in place and secured.

While the invention has been described through the presentation of a specific example of an embodiment, it is evident that, based on the knowledge provided by the present disclosure, the invention could be embodied in numerous other variations.

For example, embodiments of the invention are conceivable using other state of the art symmetrical balance coil arrangements that consist of multiple transmitter and/or multiple receiver coils that are arranged asymmetrically to achieve the null balance condition within the funnel shape configuration.

Other embodiments of the invention are also conceivable where the funnel has the shape of a skewed cone or pyramid, or where the means for reducing or eliminating the metal free zone are coils at or near the entrance and exit apertures which are actively energized by an electronic circuit, in contrast to the metallic flanges or collars which are passive carriers of induced currents. It should be understood that all such variations and combinations are considered to be within the scope of the present invention.

What is claimed is:

1. A device for detecting metal in an object under inspection, comprising:
    a metallic enclosure, having entrance and exit apertures, the apertures having cross-sectional areas of different size and defining a travel path inside the enclosure along which an object being inspected moves; and
    a coil system, comprising:
        at least one transmitter coil; and
        at least one first and at least one second receiver coil, the respective receiver coils bounding a detection zone inside the enclosure between the entrance and exit apertures; the detection zone having a cross-sectional profile that varies along the travel path;
        wherein the respective coils differ in size from each other and the at least one first receiver coil and the at least one second receiver coil are positioned at unequal distances from the at least one transmitter coil, such that, when the at least one transmitter coil is energized by an alternating electric current, the primary electromagnetic field generated thereby induces a first voltage in each of the at least one first receiver coils and a second voltage in each of the at least one second receiver coil, the first and second voltages cancelling each other out when there is no metal present in the object under inspection.

2. The device of claim 1, wherein:
    each of the at least one first receiver coils is arranged, relative to the travel path, upstream of the at least one transmitter coil; and each of the at least one second receiver coils is arranged downstream of the at least one transmitter coil.

3. The device of claim 2, further comprising:
a hollow coil former, on which each of the first and the second receiver coils and the transmitter coil are wound, the coil former made of an electrically insulating non-metallic material, an inside profile of the coil former conforms to the variable cross-sectional profile of the detection zone.

4. The device of claim 3, further comprising:
a potting compound that fills a space between the coil former and the metallic enclosure.

5. The device of claim 3, wherein:
the transmitter coil is positioned out of center between the first and second receiver coils.

6. The device of claim 5, wherein:
the transmitter coil is positioned in a central plane between the entrance aperture and the exit aperture.

7. The device of claim 5, wherein:
the transmitter coil is positioned out of center between the entrance aperture and the exit aperture.

8. The device of claim 1, wherein:
the transmitter coil is arranged nearer to the smaller of the first and second receiver coils.

9. The device of claim 1, wherein:
the detection zone has the shape of a funnel.

10. The device of claim 9, wherein:
the detection zone has a shape selected from the group consisting of: an inverted truncated cone, a section of a hyperboloid or other surface of revolution, an inverted truncated pyramid, and another continuous or multifaceted surface of rotational symmetry.

11. The device of claim 9, wherein:
the metallic enclosure has a shape that is different from the shape of the detection zone.

12. The device of claim 9, wherein:
the metallic enclosure approximately follows the shape of the detection zone, leaving a space of substantially uniform width between the coil former and the enclosure.

13. The device of claim 1, further comprising:
means for cancelling the primary field beyond a distance from the coil system.

14. The device of claim 13, wherein:
the means for cancelling the primary field comprises metallic flanges or collars that are connected to or integral with a rim of the respective entrance and exit apertures of the metallic enclosure.

15. The device of claim 13, wherein:
the means for cancelling nullifies the primary field of the transmitter coil outside of the confines of the enclosure and the primary field does not reach outside either the entrance aperture or the exit aperture.

16. The device of claim 1, further comprising:
a hollow coil former, on which each of the first and the second receiver coils and the transmitter coil are wound, the coil former made of an electrically insulating non-metallic material, an inside profile of the coil former conforms to the variable cross-sectional profile of the detection zone.

17. The device of claim 1, further comprising:
a hollow coil former, on which the first and second receiver coils are connected in series with each other, but their windings are wired with the opposite sense of rotation relative to each other, the coil former made of an electrically insulating non-metallic material, an inside profile of the coil former conforming to the variable cross-sectional profile of the detection zone.

18. The device of claim 1, wherein:
the transmitter coil is positioned out of center between the first and second receiver coils.

19. The device of claim 2, further comprising:
a hollow coil former, on which the first and second receiver coils are connected in series with each other, but their windings are wired with the opposite sense of rotation relative to each other, the coil former made of an electrically insulating non-metallic material, an inside profile of the coil former conforming to the variable cross-sectional profile of the detection zone.

* * * * *